United States Patent [19]

Gourvest et al.

[11] Patent Number: 4,988,684
[45] Date of Patent: Jan. 29, 1991

[54] NOVEL 4-ALKYLTHIO-STEROIDS

[75] Inventors: Jean-Francois Gourvest, Joinville Le Pont; Dominique Lesuisse, Paris; Daniel Philibert, La Varenne Saint Hilaire; Jean P. Vevert, Pantin, all of France

[73] Assignee: Roussel Uclaf, Paris, France

[21] Appl. No.: 454,697

[22] Filed: Dec. 21, 1989

[30] Foreign Application Priority Data

Dec. 22, 1988 [FR] France .................. 88 16993

[51] Int. Cl.$^5$ .................. A61K 31/565; A61K 31/56; C07J 1/00; C07J 31/00
[52] U.S. Cl. .................. 514/177; 514/178; 514/179; 552/511; 552/515; 552/523
[58] Field of Search .................. 514/178, 179, 177; 552/523, 515, 511

[56] References Cited

U.S. PATENT DOCUMENTS 4,322,416  3/1982  Metcalf .................. 514/177
4,810,423  3/1989  Buzzetti .................. 514/178

FOREIGN PATENT DOCUMENTS 2166742  5/1986  United Kingdom .................. 514/177

OTHER PUBLICATIONS

Faustini et al., "4-Hydroxy Derivatives . . . " CA 109:93430.

Primary Examiner—Cecilia Shen
Assistant Examiner—Celia Chang
Attorney, Agent, or Firm—Bierman and Muserlian

[57] ABSTRACT

A compound of the formula

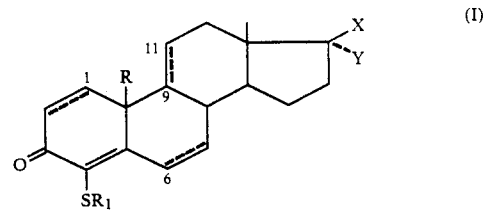

wherein R is selected from the group consisting of alkyl of 1 to 4 carbon atoms and alkenyl and alkynyl of 2 to 4 carbon atoms, $R_1$ is alkyl of 1 to 6 carbon atoms unsubstituted or substituted with at least one member of the group consisting of alkoxy and alkylthio of 1 to 4 carbon atoms, $-NO_2$, $-CN$ and halogen, X and Y together are $=O$ or Y is hydrogen and X is $-OH$, etherified $-OH$ or esterified $-OH$, the dotted lines in the 1(2), 6(7) and 9(11) positions indicate a possible double bond with the proviso that $R_1$ is alkyl of 1 to 6 carbon atoms when X and Y are $=O$ and there is a double bond in at least one of the 1(2), 6(7) and 9(11) positions having aromatase inhibiting activity.

12 Claims, No Drawings

NOVEL 4-ALKYLTHIO-STEROIDS

STATE OF THE ART

Related prior art includes German Pat. No. 1,217,375, British Pat. No. 2,166,742 and J. of Medicinal Chemistry, Vol. 29 No. 4 (1986), p. 582-584 and Vol. 28 No. 6 (1985) p. 788-795.

OBJECTS OF THE INVENTION

It is an object of the invention to provide the novel 4-alkylthio-steroids of formula I and a novel process for their preparation.

It is another object of the invention to provide novel compositions for inhibiting aromatase and a novel method of inhibiting aromatase in warm-blooded animals.

These and other objects and advantages of the invention will become obvious from the following detailed description.

THE INVENTION

The novel 4-alkyl-steroids of the invention have the formula

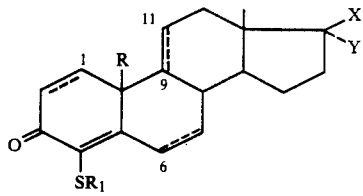

wherein R is selected from the group consisting of alkyl of 1 to 4 carbon atoms and alkenyl and alkynyl of 2 to 4 carbon atoms $R_1$ is alkyl of 1 to 6 carbon atoms unsubstituted or substituted with at least one member of the group consisting of alkoxy and alkylthio of 1 to 4 carbon atoms, $-NO_2$, $-CN$ and halogen, X and Y together are $=O$ or Y is hydrogen and X is $-OH$, etherified $-OH$ or esterified $-OH$, the dotted lines in the 1(2), 6(7) and 9(11) positions indicate a possible double bond with the proviso that $R_1$ is alkyl of 1 to 6 carbon atoms when X and Y are $=O$ and there is a double bond in at least one of the 1(2), 6(7) and 9(11) positions.

Examples of R are methyl, ethyl, propyl, butyl, isobutyl, vinyl, allyl, ethynyl, propynyl with methyl, ethyl, ethynyl or propynyl being preferred, most preferably methyl. By propynyl is meant 1- or 2-propynyl. Examples of $R_1$ are methyl, ethyl, propyl, isopropyl, butyl, isobutyl, secondary butyl, tert.-butyl pentyl, hexyl, with alkyl of 1 to 4 carbon atoms being preferred and most preferably methyl.

Examples of alkoxy and alkylthio as optional substituent on the alkyl are methoxy, methylthio, ethoxy, ethylthio propoxy and propylthio as well as n-butyl, sec-butyl or tert.-butyl oxy or thio. Alkoxy and alkylthio of 1 or 2 carbon atoms are preferred and methoxy and methylthio are even more preferred. Among the halogen atoms are fluorine, chlorine, bromine or iodine atoms with fluorine or chlorine atoms preferred.

By optionally acylated or etherified hydroxy is meant an $OR_{17}$ radical in which $R_{17}$ is hydrogen, an acyl derived from an organic carboxylic acid of 1 to 18 carbon atoms or the residue of an ether which is easily eliminated. When $R_{17}$ is acyl, $R_{17}$ preferably is the residue of a saturated or unsaturated aliphatic or cycloaliphatic acid and particularly the residue of an alkanoic acid such as for example acetic acid, propionic acid, butyric acid, isobutyric acid, valeric acid or undecylic acid, the residue of a hydroxyalkanoic acid such as for example hydroxyacetic acid, the residue of a cycloalkylcarboxylic or (cycloalkyl) alkanoic acid such as for example cyclopropylcarboxylic acid, cyclopentylcarboxylic acid or cyclohexylcarboxylic acid, cyclopentyl acetic acid or cyclohexyl acetic acid, cyclopentyl propionic acid or cyclohexyl propionic acid, the residue of a benzoic acid or of a phenylalkanoic acid such as phenyl acetic acid or phenyl propionic acid, the residue of an amino acid such as diethylamino acetic or aspartic acid or the residue of formic acid. Acetyl, propionyl or benzoyl are preferred. Among the ether radicals which are easily eliminated, there are preferred tert.-butyl, benzyl or methoxy-methyl.

It is understood that $R_1$ can be monosubstituted by one of the radicals mentioned above, as well as by the nitro and cyano radicals, but also that it can be substituted by several identical or different substituents. Among the plural substituted radicals there are preferred plural-substituted by halogen atoms such as $-CHF_2$.

Among the preferred values of $R_1$ is

in which R' is hydrogen or halogen, R" is hydrogen or alkyl of 1 to 5 carbon atoms and $R_1'$ is alkoxy or alkylthio of 1 to 4 carbon atoms, nitro or cyano or halogen.

Among the preferred products of formula I are those wherein R is methyl and those $R_1$ is selected from the group consisting of $-CH_2Hal$ or $-CHHal_2$ in which Hal is halogen, $-CH_2CN$, $-CH_2OCH_3$, $-CH_2-SCH_3$ and $-CH_2NO_2$ and more particularly $R_1$ is $-CH_2Cl$, $-CH_2F$ or $-CHF_2$ and R is methyl.

Among the specific products of formula I are 4-[(fluoromethyl)-thio]-$\Delta^4$-androstene-3,17-dione and 4-[(chloromethyl)-thio]-$\Delta^4$-androstene-3,17-dione.

The novel process of the invention for the preparation of the products of formula I comprises reacting a halide of the formula $Hal'R_1$, in which $Hal'$ is halogen with a product of the formula

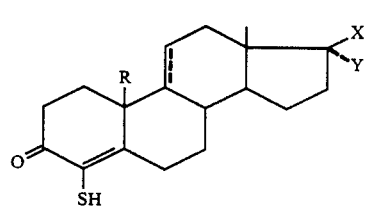

to obtain a product of the formula

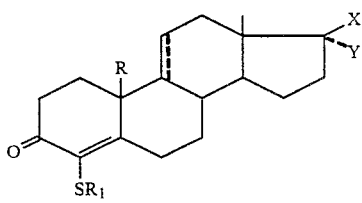

I_A corresponding to a product of formula I in which the dotted lines in position 1(2) and 6(7) are a simple bond between the carbons which carry them and if desired reacting the latter with a dehydrogenation reagent to obtain a product of the formula

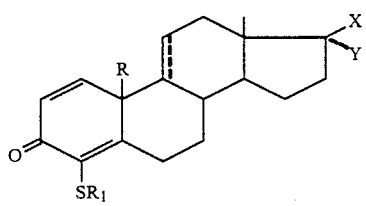

I_B corresponding to a product of formula I in which the dotted line in position 1(2) indicates the presence of a second bond between the carbons which carry it and the dotted line in position 6(7) is a simple bond and if desired, firstly a protection reagent of the 3-keto $\Delta^4$ function, and then a dehydrogenation reagent are reacted on the products of formula (I_A) or (I_B) to obtain a product of the formula

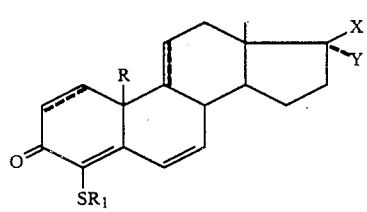

I_C corresponding to a product of formula I in which the dotted line in position 6(7) indicates the presence of a second bond between the carbons which carry them.

In a preferred mode of the process, first a strong base which can be, for example, potassium tertbutylate, sodium hydride or lithium diisopropylamide, is reacted with the product of formula II in a solvent such as tetrahydrofuran. The halide Hal'R_1 used is preferably the bromide or iodide but the chloride can also be used. The optional conversion of the products of formula I_A into products of formula I_B is preferably carried out with 2,3-dichloro-5,6-dicyano-1,4-benzoquinone (D.D.Q) and the optional conversion of the products of formula I_A or I_B into products of formula I_C is preferably carried out by the action first of an orthoformate such as ethyl orthoformate in the presence, for example, of p-toluenesulfonic acid in ethanol or a standard solvent, then by the action of chloranil in a solvent such as aqueous acetone.

The products of formula I_A in which R_1 is a non-substituted alkyl can also be prepared by reacting a product of the formula

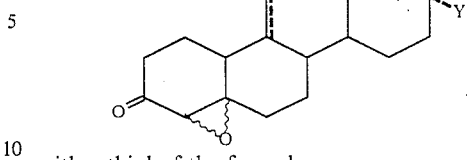

IV with a thiol of the formula

R_1' SH in which R_1' is a non-substituted alkyl in a lower alcohol. In the preferred conditions for carrying out this process, the thiol derivative is an alkali metal thiolate such as sodium methane-thiolate and the reaction is effected in methanol.

The observation according to which about 35% of breast cancers are estrogeno-dependent has led to research for ways of limiting the production of estrogens. After having used surgical methods consisting of suppressing the sources of estrogens (ovaries) or the sources of their biosynthetic precursors, androgens (suprarenal glands), efforts have been made develop less traumatic methods. (ABUL—HAJJ, Steroid Bichem., Vol. 13 (1980), 1935; BRODIE, Cancer Res., Vol. 42, (1982), p. 3312).

With regard to this, the specific inhibition of the last enzymatic stage of the aromatization of 3-keto-$\Delta^4$-androgens into phenol estrogens seems the most effective and least disturbing way. The enzyme responsible for this conversion is a mono-oxygenase known as being a cytochrome P 450: AROMATASE (BRODIE A.M.H., J. Endocrinol. Invest., Vol. 2 (1979), p 445) which requires oxygen and NADPH (reduced Nicotinamide Adenine Dinucleotide phosphate) to effect the aromatization of androgens into estrogens.

Based on another mechanism, other authors (for example MARCOTTE et al, Biochemistry, Vol. 21, (1982), 2773, FLYNN et al Biochem. Biophys. Res. Com., Vol. 103 (1981), p 713) have put forward suicide inhibitors for Aromatase. Competitive inhibitors such as Aminogluthetimide have also been put forward for the treatment of metastasic breast cancer. This product, however, has been shown not to be specific for Aromatase as in effect, it attacks enzymatic processes other than that leading from androgens to estrogens.

The novel aromatase inhibiting compositions of the invention are comprised of an effective aromatase inhibiting amount of at least one compound of formula I and an inert pharmaceutical carrier. The compositions may be in the form of tablets, dragees, capsules, suppositories, gels, patches, creams, ointments, ovules and injectable solutions or suspensions.

Examples of suitable excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying agents and preservatives.

The compositions have a specific activity of the type of suicide inhibitors of aromatase (cytochrome P450 aromatase) and this makes the compositions useful for the treatment of cancers of the breast, endometrium, ovary and pancreas, gynecomastia, benign disorders of the breast, endometriosis, polycystic affections of the ovary, prostatic hyperplasia, and more generally in the treatment of hyperestrogenemia.

The novel method of the invention for inhibiting aromatase activity in warm-blooded animals, including humans, comprises administering to warm-blooded animals an aromatase inhibiting effective amount of at least one compound of formula I. The compounds may be administered orally, rectally, parenterally or topically and the usual daily dose is 0.1 to 50 mg/kg depending on the condition treated, specific compound and method of administration. It can be preferably 0.5 to 10 mg/kg per day per os in the adult.

Some of the products of formulae II and IV are known. Thus, 4-thioandrostene-dione and the corresponding 4,5-epoxy derivative used in the examples are described in J. Med. Chem., Vol. 28, p. 788 (1985) and J. Med. Chem., Vol. 29, p. 582 (1986), The products of formulae II and IV which are not known can be prepared as follows;

A product of formula III:

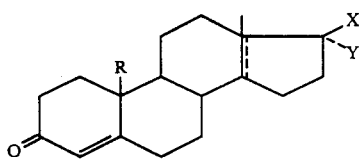

III is reacted with an epoxidation agent such as hydrogen peroxide in the presence of sodium hydroxide in a solvent mixture such as methylene chloride and methanol or tert-.butyl peroxide in the presence of triton B in methanol to obtain a product of the formula

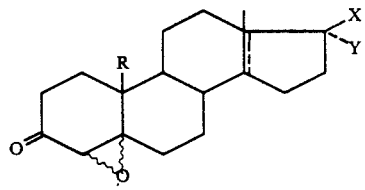

IV which is reacted with thioacetic acid in a solvent such as dioxane or methanol, then is reacted either with an acid such as hydrochloric acid in a solvent such as methanol, tetrahydrofuran, acetone or an alkali metal alcoholate such as sodium methylate in methanol or potassium hydroxide in methanol to obtain the product of formula II.

The products of formula III are described in the literature or can be obtained by methods known to an expert. Products of formula III possessing a double bond in the 9(11) position are described in the following references: R=alkyl: French Pat. No. 1,255,101; British Pat. No. 1,081,307; Bull. Soc. Chim-Fr. 1970 (7) pp 2556–64: R=alkenyl: U.S. Pat. No. 3,284,448. Steroids, 1981, 37 (4), 361–82: R=alkynyl: German Pat. No. 3,644,358, J. Biol. Chem., 1981, 256 (3) 1076-9.

Products of formula III not possessing a double bond in the 9(11) position are described in the following references: R=alkyl, alkenyl, alkynyl and -CN: Steroids 1982, 39 (3) pp 325–44. R=alkynyl: U.S. Pat. No.3,218,316.

In addition to the products described in the examples, the following products constitute products within the scope of the present invention, the substituents R, $R_1$, X and Y are those indicated formula I.

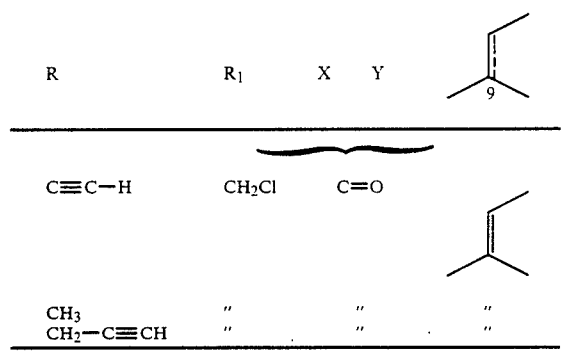

| R | $R_1$ | X | Y | |
|---|---|---|---|---|
| C≡C—H | $CH_2Cl$ | C=O | | |
| $CH_3$ | " | " | " | |
| $CH_2$—C≡CH | " | " | " | |

In the following examples there are described several preferred embodiments to illustrate the invention. However, it should be understood that the invention is not intended to be limited to the specific embodiments.

EXAMPLE 1

4-fluoromethylthio-$\Delta^4$-androstene-3,17-dione

STEP A: Bromofluoromethane 25 g of fluoroacetic acid, 250 ml of acetone and 50 ml of water were mixed together and 25 ml of ammonia 22° Be were added over 5 minutes. The mixture was stirred for 20 minutes at ambient temperature and was evaporated to dryness under reduced pressure. The residue was taken up in 50 ml of acetone and 20 ml of water and evaporated to dryness again. The solid residue was suspended in 500 ml of acetone and 100 ml of water were added. After cooling to 5° C., 54.4 g of silver nitrate were added with stirring and the mixture was stirred for one hour at 0°–5° C., filtered, washed with acetone, then with ether, and dried under reduced pressure at 70° C. shaded from the light to obtain 57 g of silver fluoroacetate which was used as is for the following reaction. 6.3 g of the silver salt, 100 ml of carbon tetrachloride and 1.8 ml of bromine (0.031 mm) were mixed together and stirred at reflux (about 64° C.) for 2 hours 30 minutes until all the $CO_2$ was released followed by cooling to 0° C. to obtain the desired product.

STEP B: 4-(fluoromethyl)-thio-$\Delta^4$-androstene-3,17-dione 1 g of potassium tertbutylate was added at 0° C. to a solution of 2 g of 4-thio-$\Delta^4$-androstene-3,17-dione in 80 ml of tetrahydrofuran and after stirring for 30 minutes at 0° C., bromofluoromethane was passed through the thiolate solution for 2 hours at 20° C. using nitrogen as the carrier gas. The reaction medium was poured into 80 ml of a saturated solution of ammonium chloride and 120 ml of dichloromethane. Extraction was carried out with dichloromethane, and the extracts were dried and concentrated to dryness. The crude product was chromatographed on silica (eluant: ethyl acetate-hexane 3-7) to obtain the expected product (Rf.=0.56, in AcOEt-hexane 1-1). The product was dissoved in dichloromethane and treated hot with active charcoal to obtain 457 mg (21%) of a yellow oil which crystallized. Crystallization from diethyl ether provided 210.6 mg of the expected product melting at 129° C.

Analysis: $C_{20}H_{27}O_2SF$:

Calculated: %C 68.54 %H 7.76 %S 9.15 %F 5.42,

Found 68.8 8.0 9.0 5.2.
NMR Spectrum CDCl$_3$ (300 MHz):
0.93 (18-Me), 1.28 (19-Me), 3.77 (dt, H6eq.),
5.49 (d, SCH$_2$F, J=53 Hz).
IR Spectrum (CHCl$_3$):
1735 cm$^{-1}$ (17-ketone), 1675 and 1560 cm$^{-1}$ (3-ketone).

EXAMPLE 2

4-Chloromethylthio-Δ$^4$-androstene-3,17-dione 1 g of 4-thio-Δ$^4$-androstene-3,17-dione and 50 ml of tetrahydrofuran were mixed together at 0° C. and 422.6 mg of potassium tertbutylate were added. The solution was stirred for 15 minutes at 0° C. and 0.43 mg of bromo-chloromethane were then added. The mixture was stirred for 15 minutes at ambient temperature and 10 ml of a saturated solution of ammonium chloride were added. The mixture was extracted with dichloromethane and the organic extracts were dried and concentrated to dryness. The residue was chromatographed (eluant mixture: AcOEt-hexane 3-7 then 1-1) to obtain 100 mg (9.6%) of a first fraction (Rf=0.63 in AcOEt-hexane 1-1) which was Δ$^{3,5}$ androstadieno-[4,3-d][1,3-oxathiole]-17-one. The following fraction (Rf=0.48), after crystallization from ethyl ether, provided 420 mg (36%) of the expected product melting at 174° C.

Analysis: C$_{20}$H$_{27}$O$_2$SCl:
Calculated: %C 65.5 %H 7.42 %S 8.74,
Found: 65.8 7.7 8.2.
NMR Spectrum (CDCl$_3$, 90 MHz): 0.96 (s, 18-Me),
1.3 (s, 19-Me), 3.65–3.81 (m, H6), 4.81 (s, CH$_2$S).
IR Spectrum (CHCl$_3$):
1734 cm$^{-1}$ (17-ketone), 1675, 1555 (conjugated ketone),
Mass Spectrum: 366 (M+), 330 (M-CHl), 315, 300.
Analyses of Δ$^{3,5}$androsta-dieno-[4,3-d][1,3-oxathiol]-17-one
NMR Spectrum (CDCl$_3$, 90 MHz):
0.92 (s, 18-Me), 1.03 (s, 19-Me), 5.16 (H5), 5.51 (CH$_2$S).
IR Spectrum
1734 (17-ketone), 1657, 1634 (conjugated system).

EXAMPLE 3

4-(methylthio)-methylthio-Δ$^4$-androstene-3,17-dione 1 g of 4-thio-Δ$^4$-androstene-3,17-dione and 40 ml of tetrahydrofuran were mixed together, and after the mixture was cooled to 0° C., 387 mg of potassium tert-butylate were added at 0° C. The mixture was stirred for 30 minutes at 0° C. and then 0.313 ml of chloromethyl thiomethyl ether were added. The mixture was stirred for 30 minutes at ambient temperature and was poured into 40 ml of a saturated solution of ammonium chloride and 60 ml of dichloromethane. After extraction with dichloromethane, the extracts were dried and concentrated. The crude product was chromatographed on silica (eluant: AcOEt-hexane 3-7) to obtain 560 mg of the expected product in the form of a yellow oil. Crystallization from diethyl ether provided 260 mg of the expected product.

Analysis: C$_{21}$H$_{30}$O$_2$S$_2$:
Calculated: %C 66.62 %H 7.99 %S 16.94,
Found: 66.7 8.0 16.6.
NMR Spectrum (CDCl$_3$, 300 MHz):
0.93 (18-Me), 1.28 (19-Me), 2.14 (s,SME), 3.82 (AB, SCH$_2$S).

IR Spectrum (CHCl$_3$):
1735 and 1406 cm$^{-1}$ (17-ketone), 1673 and 1557 (3-ketone).

EXAMPLE 4

4-Methoxymethyl-thio-Δ$^4$-androstene-3,17-dione 1 g of 4-thio-Δ$^4$-androstene-3,17-dione and 40 ml of tetrahydrofuran were mixed together and after the mixture was cooled to 0° C., 387 mg of potassium tertbutylate were added at 0° C. The mixture was stirred for 30 minutes at 0° C., then 0.308 ml of bromomethyl methyl ether were added. The mixture was stirred for 30 minutes at ambient temperature and poured into 40 ml of a saturated solution of ammonium chloride and 60 ml of dichloromethane. The aqueous phase was extracted with dichloromethane, dried and concentrated. The crude product was chromatographed on silica (eluant: AcOEt-hexane 3-7) to obtain the product (Rf=0.5 AcOEt-hexane 1-1) in the form of a yellow oil which was crystallized from diethyl ether to obtain 109 mg of expected product.

Analysis: C$_{21}$H$_{30}$O$_3$S:
Calculated: %C 69.57 %H 8.34 %S 8.94,
Found: 69.5 8.1 8.6.
NMR Spectrum (CDCl$_3$, 300 MHz): 0.93 (18-Me),
1.26 (19-Me),
3.74 (s, OMe) 3.76 (ddd, H6eq.), 4.95 and 4.73 (2d, SCH$_2$O).
IR Spectrum (CHCl$_3$):
1735 cm$^{-1}$ (17-ketone) 1674 and 1558 (3-ketone).

EXAMPLE 5

4-difluoromethylthio-Δ$^4$-androstene-3,17dione 1 g of 4-thio-Δ$^4$-androstene-3,17-dione and 20 ml of tetrahydrofuran were mixed together and after the mixture was cooled to 0° C., 422.6 mg of potassium tertbutylate were added at 0° C. The mixture was stirred for 5 minutes at 0° C. then a large amount of freon was introduced all at once. The excess freon filled the empty balloon-flask attached to the apparatus and the mixture was stirred for 12 hours at ambient temperature. After concentration, chromatography was carried out on silica (eluant: AcOEt-hexane 3-7, followed by 1-1) to obtain 610 mg of expected product. Crystallization from ethyl acetate provided 400 mg of the expected compound in crystals melting at 129° C.

Analysis: C$_{20}$H$_{26}$O$_2$SF$_2$:
Calculated: %C 65.19 %H 7.11 %S 8.7 %F 10.3,
Found: 65.4 7.2 8.4 9.6–9.9.
NMR Spectrum (CDCl$_3$, 250 MHz):
0.93 (s, 18-Me), 1.29 (s, 19-Me), 6.91 (t, J=59 Hz, CHF$_2$)
3.68 (H6).
IR Spectrum (CHCl$_3$):
1735 cm$^{-1}$ (17-ketone), 1680, 1559 (conjugated ketone), 1050–1070 (C-F
Mass Spectrum: 368 (M+), 348 (M-F), 317 (M-CHF$_2$), 285 (M-SCHF$_2$)
267.

EXAMPLE 6

[(4-androstene-4-yl-3,17-dioxo-Δ$^4$-)-thio]-acetonitrile 1 g of 4-thio-Δ$^4$-androstene-3,17-dione and 40 ml of tetrahydrofuran were mixed together and cooled to 0° C. and at this temperature, 387 mg of potassium tert.butylate were added. The mixture was stirred for 30 minutes at 0° C. and then, 0.263 mg of bromo-acetonitrile were added followed by stirring for 30 minutes at ambient temperature. The mixture was poured into 40 ml of a saturated solution of ammonium chloride and 60 ml of dichloromethane. The aqueous phase was extracted with dichloromethane and the organic phase was dried and concentrated to dryness. The crude product was chromatographed on silica (eluant: AcOEt-hexane 3-7) to obtain 640 mg of the expected product in the form of an oil. Crystallization from diethyl ether provided 260 mg of the expected product.

Analysis: $C_{21}H_{27}O_2NS$:
Calculated: %C 70.55 %H 7.61 %S 8.97 %N 3.92;
Found: 70.7 7.7 8.7 3.9.
NMR Spectrum (CDCl$_3$, 300 MHz):
0.93 (18-Me), 1.31 (19-Me), 3.51 and 3.60 (2d, J=17 Hz,
SCH$_2$CN) 3.75 (dt, H6eq.).
IR Spectrum (CHCl$_3$):
2232 cm$^{-1}$ (CN), 1735 cm$^{-1}$ (17-ketone) 1675 and 1556 (3-ketone).

EXAMPLE 7

4-nitromethyl-thio-$\Delta^4$-androstene-3,17-dione 1 g of 4-thio-$\Delta^4$-androstene-3,17-dione and 40 ml of tetrahydrofuran were mixed together and cooled to 0° C. and at this temperature, 387 mg of potassium tert-.butylate were added. The mixture was stirred for 30 minutes at 0° C. and 0.263 ml of bromonitromethane were added followed by stirring for 30 minutes at ambient temperature. The mixture was poured into 40 ml of a saturated solution of ammonium chloride and 60 ml of dichloromethane and the aqueous phase was extracted with dichloromethane. The organic phaase was dried and coccentrated and the crude product was chromatographed on silica (eluant : AcOEt -hexane 3-7) to obtain 134 mg of the expected product
NMR Spectrum (CDCl$_3$, 200 MHz):
0.93 (18-Me), 1.28 (19-Me), 3.61 (ddd, H6eq.), 5.34 (AB, J=12.5 Hz, SCH$_2$NO$_2$).
IR Spectrum (CHCl$_3$)
1735 cm$^{-1}$ (17-ketone) 1677 and 1553 (3-ketone).

EXAMPLE 8

4-(methylthio)-$\Delta^{4,9(11)}$androstadien-3,17-dione 39.2 ml of 30% hydrogen peroxide were added to 23 g of $\Delta^{4,9(11)}$-androstadien-3,17-dione in solution in 200 ml of methylene chloride which had added to it 2 liters of methanol. The mixture was stirred for 30 minutes at ambient temperature followed by cooling to 0° C. 8.5 ml of 4M sodium hydroxide were added over 30 minutes and the mixture was stirred for 12 hours at 4° C. The reaction was neutralized by the addition of N hydrochloric acid and the solvent was partially evaporated to about 200 ml. 200 ml of water were added and the precipitate obtained was filtered. After washing with ether, 16.8 g of the 4,5-epoxide product were obtained with an Rf=0.44 (cyclohexane -ethyl acetate 1-1). 232 mg of sodium methanethiolate were added to 1 g of the epoxide in 400 ml of tetrahydrofuran, and the mixture was stirred for one hour at ambient temperature. The reaction mixture was poured into water and the precipitate was filtered to obtain 420 mg of crude product. The filtrate was extracted with methylene chloride and the organic phase was dried and concentrated to dryness to obtain 600 mg of crude product. The combined 2 lots of crude product were purified by chromatography under pressure (eluant: cyclohexane-ethyl acetate 8-2) to obtain 500 mg of expected product with Rf=0.51 (ethyl acetate-cyclohexane 1-1).

| IR Spectrum (CHCl$_3$) | |
| --- | --- |
| C=O (17-keto | 1735 cm$^{-1}$ |
| conjugated ketone 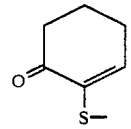 | 1673 cm$^{-1}$ 1556 cm$^{-1}$ |

EXAMPLE 9

4-methylthio-$\Delta^{4,5,9(11)}$-androstatrien-3,17-dione 300 mg of the product of Example 8 in 7.5 ml of ethanol and 1.1 ml of ethyl orthoformate were stirred in the presence of 1.5 mg of p-toluenesulfonic acid for 2 hours at ambient temperature. Then 0.4 ml of triethylamine were added and the reaction medium was poured into 50 ml of a saturated aqueous solution of sodium bicarbonate, and extracted with methylene chloride. The extracts were dried, 0.5 ml of triethylamine was added and the solvent was eliminated to obtain 200 mg of 3-ethoxy product. 250 mg of chloranil were added to the 200 mg of product in 9.3 ml of an acetone-water mixture (95-5) and the mixture was stirred for 16 hours at ambient temperature and poured into 10 ml of a 10% solution of sodium thiosulfate. 10 ml of an aqueous solution of sodium bicarbonate were added and the mixture was stirred for one hour at ambient temperature. After extraction with methylene chloride and drying, the solvent was evaporated. The residue was purified by chromatography under pressure (eluant: ethyl acetate-cyclohexane 2-8) to obtain 100 mg of the expected product with a Rf=0.61 (ethyl acetate-cyclohexane 1-1).

| IR Spectrum (CHCl$_3$) | |
| --- | --- |
| (17-keto) | 1735 cm$^{-1}$ |
| conjugated ketone | 1667 cm$^{-1}$ 1616 cm$^{-1}$ 1525 cm$^{-1}$ |

EXAMPLE 10

4-methylthio-$\Delta^{1,4,9(11)}$-androstatrien-3,17-dione 172 mg of 2,3-dichloro-5,6-dicyano-1,4-benzoquinone (D.D.Q.) were added to 100 mg of the product of Example 8 in 30 ml of dioxane and the mixture was refluxed for 16 hours. The solvent was evaporated and the D.D.Q. was eliminated by filtration. The residue was purified by chromatography under pressure on silica (eluant: ethyl acetate-cyclohexane 2-8) to obtain 30 mg of the expected product with a Rf=0.49 (ethyl acetate-cyclohexane 1-1).

EXAMPLE 11

4-methylthio-$\Delta^{1,4,6,9(11)}$-androstatetraen-3,17-dione 5.5 g of D.D.Q. were added to 3.2 g of the product of Example 8 in 350 ml of dioxane and the mixture was stirred for 24 hours at ambient temperature, then for 12 hours at reflux. The dioxane was evaporated, followed by filtering on silica, and the product was taken up in 350 ml of dioxane. 5.5 g of D.D.Q. were added and the mixture was refluxed again for 12 hours. The dioxane was evaporated, followed by filtering on silica to eliminate the D.D.Q., and purification by chromatography on silica (eluant: 8-2 cyclohexane-ethyl acetate) to obtain 2.5 g of crude product which was crystallized from ether. The filtrate obtained yielded 2.31 g of a mixture (1-1) of -$\Delta^{1,4,6,9(11)}$-tetraene product and -$\Delta^{1,4,9(11)}$-triene product.

Analysis: $C_{20}H_{22}O_2S$:
Calculated: %C 73.5 %H 6.85 %S 9.82,
Found: 73.4 6.8 9.8.

EXAMPLE 12

4-[(fluoromethyl)-thio]-$\Delta^{4,6,9(11)}$androstatrien-3,17-dione 160 mg of m-chloroperbenzoic acid were added at 0° C. to 300 mg of the product of Example 9 in 10 ml of methylene chloride and the mixture was stirred for 30 minutes at 0° C. A further 16 mg of acid were added followed by stirring for 10 minutes at 0° C. and then 5 ml of a saturated aqueous solution of sodium bicarbonate were added. Extraction was carried out with methylene chloride, and the extracts were dried and concentrated to dryness to obtain 310 mg of sulfoxide with a RF=0.06 (ethyl acetate-cyclohexane 1-1). 170 mg of the sulfoxide in 5 ml of chloroform were cooled to −78° C. and 0.14 ml of diethylaminosulfide trifluoride were added. The mixture was stirred for 7 hours at ambient temperature, then for 16 hours at reflux. After cooling, 5 ml of aqueous solution of sodium bicarbonate were added, followed by extraction with methylene chloride, drying, and evaporation of the solvent. The residue was purified by chromatography on silica under pressure (eluant: ethyl acetate-cyclohexane 3-7) to obtain 75 mg of the expected product with a Rf=0.6 (ethyl acetate-cyclohexane 1-1).

Pharmaceutical compositions

Tablets were prepared containing 50 mg of the product of Example 1 and sufficient excipient of talc, starch, magnesium stearate for a tablet of 120 mg.

PHARMACOLOGICAL STUDY

Inhibition dependent on the concentration (measurement of the $IC_{50}$=concentration of the inhibitor necessary to reduce the enzymatic activity by 50%). Human placentas were used which one hour or more after birth were washed, perfused with physiological serum (5 liters) via the umbilical vein and then frozen at −40° C.

(1) Obtaining placentary microsomes

The placentas were thawed at 4° C., then homogenized (1:3) in a 10 mM phosphate buffer, pH=7.0, containing 100 mM of potassium chloride (KCl), 10 mM of dithiothreitol (DTT), 10 mM of ethylenediaminetetraacetic acid (EDTA), 40 mM of nicotinamide and 250 mM of sucrose. The homogenates were then subjected to various stages of centrifugation until the "9000 g" supernatant was obtained (corresponding to cytosol and to endoplasmic reticulum). This supernatant was then subjected to an ultracentrifugation stage (90 minutes, 105,000 g) to obtain the microsome deposit. The microsomes were then resuspended in a 50 mM phosphate buffer, pH=7.4, containing 100 mM KCl, 1 mM EDTA, 1 mM DTT and glycerol (10%). The microsome suspension was then divided into equal parts and the fractions were frozen at the temperature of liquid nitrogen. The protein concentration of the microsome suspension was determined by the BRADFORD method (BRADFORD, Anal. Biochem., Vol. 72 (1976), p. 248).

(2) Measurement of the $IC_{50}$ of each inhibitor

To 960 microliters of phosphate buffer (50 mM, pH=7.2). 2.5 mM of glucose-6-phosphate and containing 0.16 international unit of glucose-6-phosphate dehydrogenase (G-6-PDH), the following were added in this order:

(1) —10 microliters of inhibitor dissolved in dimethylsulfoxide (DMSO) to give final concentrations of from $10^{-6}M$ to $10^{-9}M$.

(2) —10 microliters of substrate of 60 nM Androstenedione dissolved in ethanol and containing 1-2-($^3H$)-Androstene-dione in a known isotopic dilution (200,000 disintegrations per minute).

(3) —10 microliters of microsome suspension equivalent to 25 micrograms of proteins per test.

The enzymatic reaction was then very quickly started by the addition of 10 microliters of reduced nicotinamide adenine dinucleotide phosphate (NADPH) dissolved in water. After stirring, each test was incubated at 37° C. for 10 minutes. The reaction was then stopped by the addition of chloroform (4 ml). After vigorous stirring of the tubes, they were decanted and centrifuged at 4° C. for 10 minutes at a speed of 3000 rpm (rotations per minute), that is 600×g. After centrifugation, and for each tube, 100 microliters of supernatant was removed and counted in the presence of scintillating liquid.

This method is derived from the processes described by REED et al., (J. Biol. Chem., Vol. 251, (1976), p. 1625) and THOMPSON et al., (J. Biol. Chem., Vol. 249, (1974), p. 5364). The enzymatic activity (aromatase) was proportional to the percentage of tritium released in the form of tritiated water ($^3H_2O$) during the reaction. The inhibition obtained for each concentration of each inhibiting product of the invention was calculated as a percentage of the controls (100% arbitrary obtained in the absence of any inhibitor). The $IC_{50}$ was equal to the concentration of inhibitor necessary to decrease by 50% the enzymatic activity. The $IC_{50}$ values obtained for the inhibiting products of the invention were:

Product of Example 1: $IC_{50}$=0.07 micromole
Product of Example 2: $IC_{50}$=0.075 micromole.

Various modifications of the products and method of the invention may be made without departing from the spirit or scope thereof and it is to be understood that the invention is intended to be limited only as defined in the appended claims.

What we claim is:

1. A compound of the formula

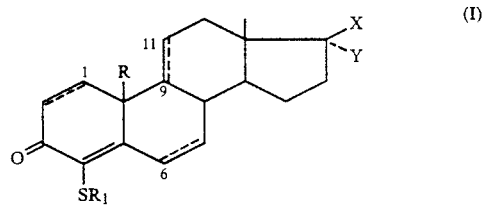

wherein R is selected from the group consisting of alkyl of 1 to 4 carbon atoms and alkenyl and alkynyl of 2 to 4 carbon atoms, $R_1$ is alkyl of 1 to 6 carbon atoms substituted with at least one member of the group consisting of alkoxy and alkylthio of 1 to 4 carbon atoms, $-NO_2$, $-CN$ and halogen, X and Y together are $=O$ or Y is hydrogen and X is $-OH$, etherified $-OH$ or esterified $-OH$, the dotted lnes in the 1(2), 6(7) and 9(11) positions indicate a possible double bond.

2. A compound of claim 1 wherein R is methyl and $R_1$ is selected from the group consisting of $-CH_2CN$, $-CH_2OCH_3$, $-CH_2SCH_3$, $-CH_2NO_2$, $-CH_2Hal$ and $-CHHal_2$ and Hal is halogen.

3. A compound of claim 1 wherein R is methyl and $R_1$ is selected from the group consisting of $-CH_2Cl$, $-CH_2F$ and $-CHF_2$.

4. A compound of claim 1 selected from the group consisting of 4-(fluoromethylthio)-$\Delta^4$-androstene-3,17-dione and 4-(chloromethylthio)-$\Delta^4$-androstene-3,17-dione.

5. A composition for inhibiting aromatase comprising an effective amount of at least one compound of claim 1 to inhibit aromatase and an inert pharmaceutical carrier.

6. A composition of claim 5 wherein R is methyl and $R_1$ is selected from the group consisting of $-CH_2CN$, $-CH_2OCH_3$, $CH_2SCH_3$, $-CH_2NO_2$, $-CH_2Hal$ and $-CHHal_2$ and Hal is halogen.

7. A composition of claim 5 wherein R is methyl and $R_1$ is selected from the group consisting of $-CH_2Cl$, $-CH_2F$ and $CHF_2$.

8. A composition of claim 5 wherein the active compound is selected from the group consisting of 4-(fluoromethylthio)-$\Delta^4$-androstene-3,17-dione and 4-(chloromethylthio)-$\Delta^4$-androstene-3,17-dione.

9. A method of inhibiting aromatase in warm-blooded animals comprising administering to warm-blooded animals an amount of at least one compound of claim 1 sufficient to inhibit aromatase.

10. A method of claim 9 wherein in the active compound, R is methyl and $R_1$ is selected from the group consisting of $-CH_2CN$, $-CH_2OCH_3$, $-CH_2SCH_3$, $-CH_2NO_2$, $-CH_2Hal$ and $-CHHal_2$ and Hal is halogen.

11. A method of claim 9 wherein in the active compound R is methyl and $R_1$ is selected from the group consisting of $-CH_2Cl$, $-CH_2F$ and $CHF_2$.

12. A method of claim 9 wherein the active compound is selected from the group consisting of 4-(fluoromethylthio)-$\Delta$-(chloromethylthio)-$\Delta^4$-androstene-3,17-dione.

* * * * *